United States Patent [19]

Coonan, III

[11] Patent Number: 5,108,456
[45] Date of Patent: Apr. 28, 1992

[54] PROSTHETIC APPLIANCE

[76] Inventor: Thomas J. Coonan, III, 3145 Iris Ct., Northbrook, Ill. 60062

[21] Appl. No.: 646,278

[22] Filed: Jan. 28, 1991

[51] Int. Cl.⁵ .............. A61F 2/60; A61F 2/74
[52] U.S. Cl. .................... 623/37; 623/26; 623/33; 623/36
[58] Field of Search .............. 623/34, 35, 33, 36, 623/37, 26, 57

[56] References Cited

U.S. PATENT DOCUMENTS

| | | | |
|---|---|---|---|
| 1,057,562 | 4/1913 | LaPoint . | |
| 1,893,853 | 1/1933 | Tullis | 623/37 |
| 2,634,424 | 4/1953 | O'Gorman . | |
| 3,671,980 | 6/1972 | Baird . | |
| 3,889,301 | 6/1975 | Bonner, Sr. . | |
| 4,300,245 | 11/1981 | Saunders | 623/37 X |
| 4,432,101 | 2/1984 | Johnson | 623/37 |
| 4,655,779 | 4/1987 | Janowiak | 623/37 |
| 4,923,475 | 5/1990 | Gosthnian et al. | 623/37 |

FOREIGN PATENT DOCUMENTS

| | | | |
|---|---|---|---|
| 0019612 | 11/1980 | European Pat. Off. | 623/37 |
| 2729800 | 1/1979 | Fed. Rep. of Germany | 623/37 |
| 3607003 | 10/1986 | Fed. Rep. of Germany | 128/80 C |
| 2506603 | 12/1982 | France | 128/80 R |
| 0425629 | 4/1974 | U.S.S.R. | 623/37 |
| 0731963 | 5/1980 | U.S.S.R. | 623/35 |

Primary Examiner—Randall L. Green
Assistant Examiner—David H. Willse
Attorney, Agent, or Firm—Lee, Mann, Smith, McWilliams, Sweeney & Ohlson

[57] ABSTRACT

A prosthetic appliance for residual limb is disclosed comprising a prosthesis member having a cavity defined by side walls formed of a rigid molded material. A separate removable molded socket member formed of a flexible material is nested within cavity of the prosthesis member and is adapted to receive the residual limb. Several separate, independently inflatable bladders preferably attached to the exterior of the socket member, when inflated, act against the rigid side walls of the prosthesis member to resiliently force discrete portions of the socket member side walls inwardly to grip the residual limb. An inflation control means is provided in the form of at least one manually operable air pump and one or more manually operable air valves, one for each of said bladders, for selectively inflating the associated bladder separately and independently from the other bladders, so that the gripping pressure of the residual limb at each discrete portion of the socket member may be adjusted separately and independently by both the air pump and the air valves.

3 Claims, 2 Drawing Sheets

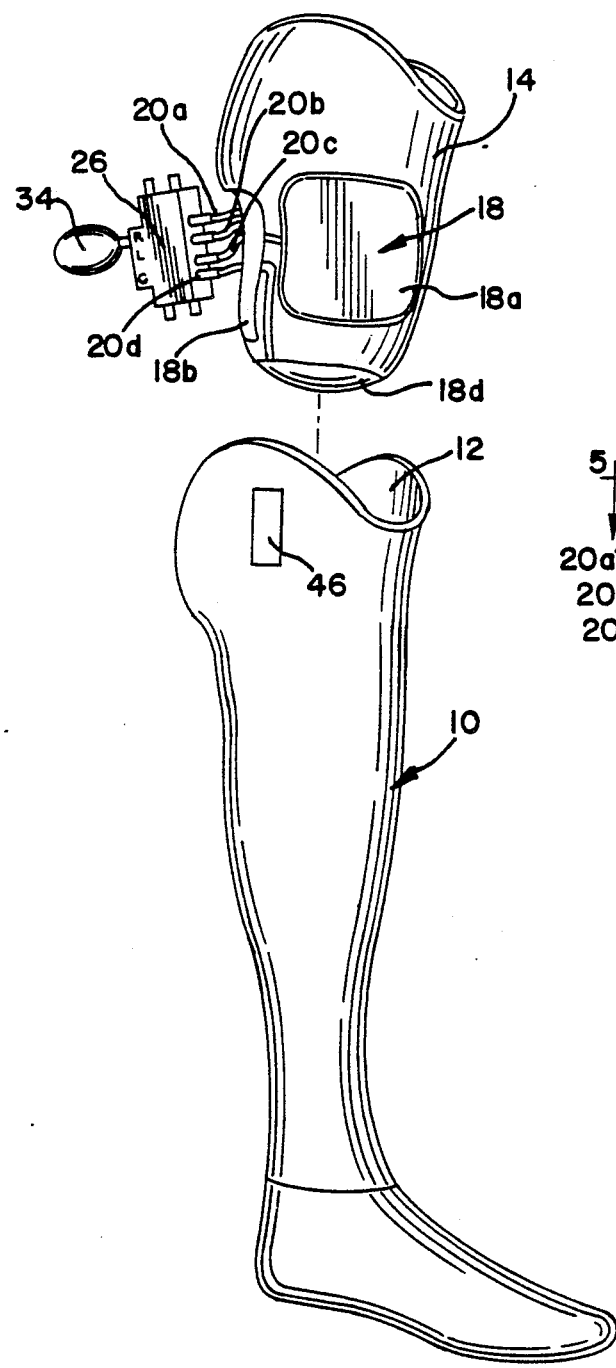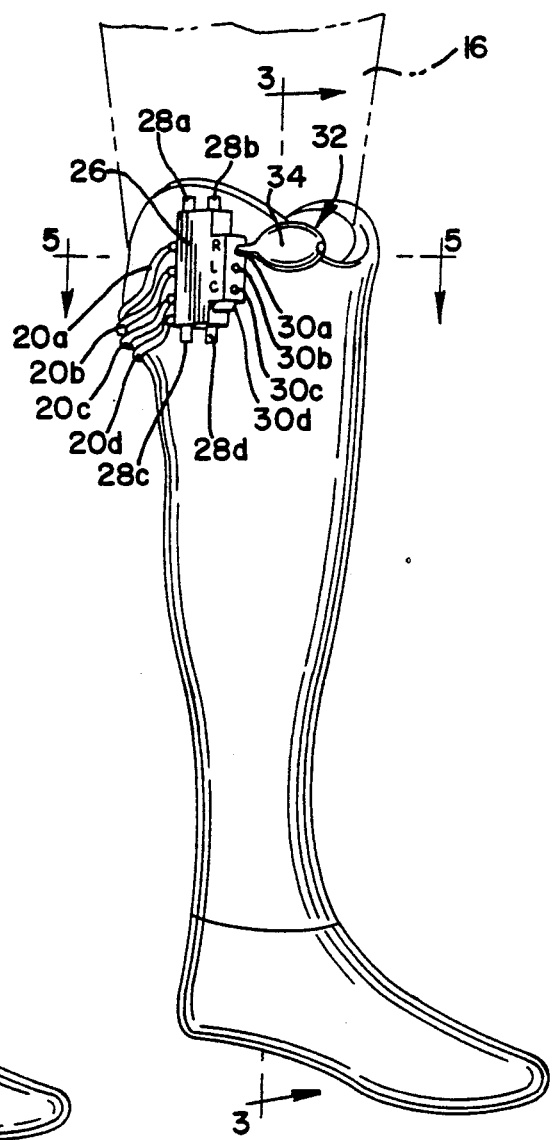

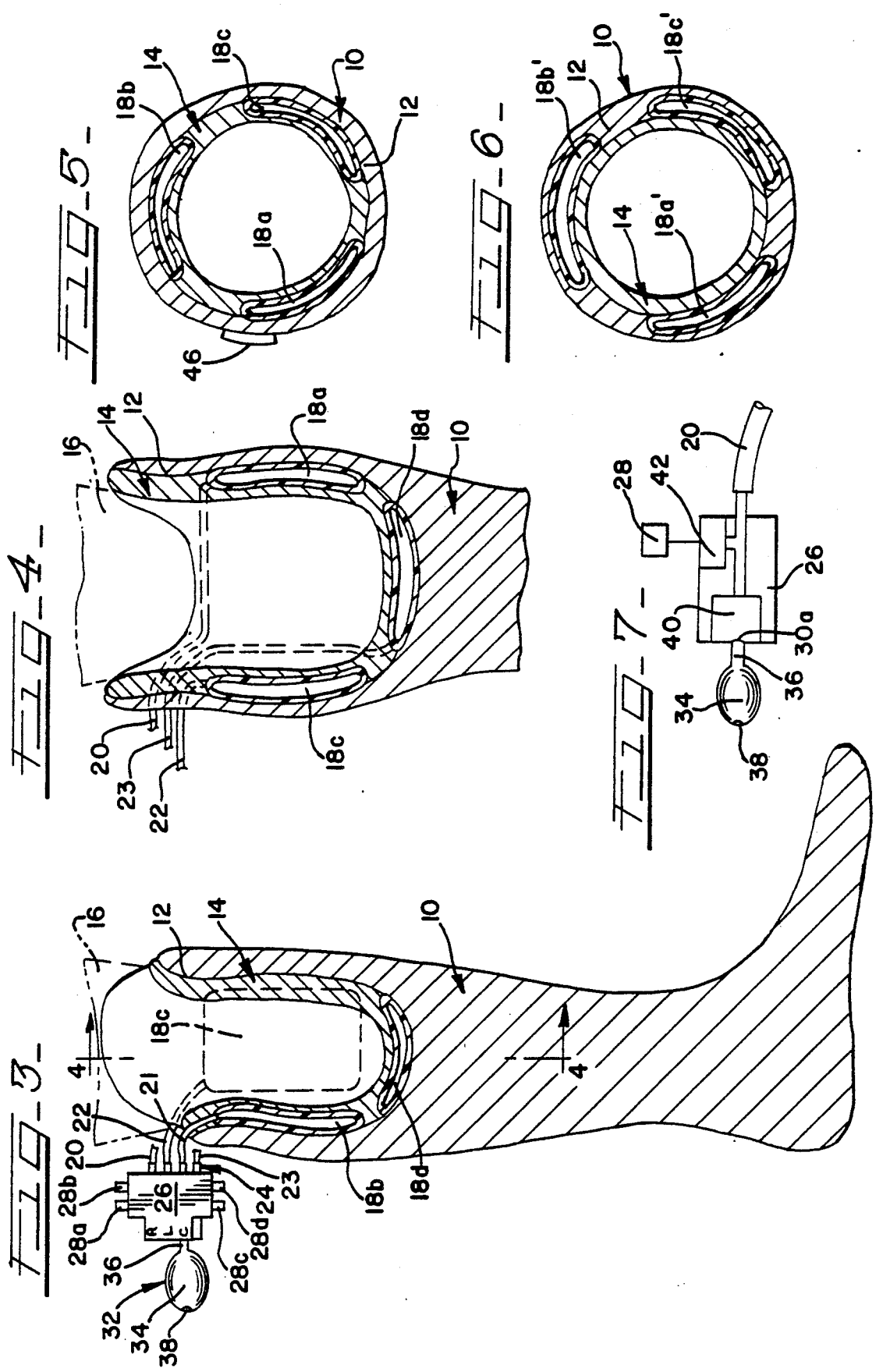

5,108,456

PROSTHETIC APPLIANCE

This invention relates to a prosthetic appliance for amputees and, more particularly, an assembly for an artificial arm or leg which permits the adjustment of pressure points for improved comfort.

BACKGROUND OF THE INVENTION

One of the most difficult problems for an amputee is obtaining a prosthesis, i.e., an artificial arm or leg, which can be worn comfortably over a long period of time. The process of making an artificial limb is quite time consuming and involves a considerable amount of fitting and adjusting. The prosthesis must be carefully fitted to the amputess residual limb, and it must be adjusted in its design to keep the weight off of the pressure-sensitive areas while permitting dynamic movement of the prosthesis and a firm attachment to the residual limb. Moreover, the residual limb varies in shape and size over a period of time because of shrinking and swelling. Size changes are common and may be caused by many factors, including heat, retention of body fluids and weight gain or loss.

Various suggestions have been made to accommodate size and shape changes and to improve the comfort of the amputee. U.S. Pat. No. 1,057,562 discloses an inflatable wrap around sleeve placed between a pair of stump socks and providing a cushion between the residual limb and the shell of the prosthesis. U.S. Pat. No. 2,634,424 discloses an inflatable socket having a series of interconnected communicating compartments. Similar inflatable sockets are shown in U.S. Pat. Nos. 3,889,301 and 4,300,245. U.S. Pat. No. 1,893,853 shows an inflatable tube mounted in the wall of the socket acting against the fabric sleeve covering the residual limb, and U.S. Pat. No. 4,655,779 discloses an inflatable socket which is inflated by means of a finger pump.

The problem with each of these prior art devices is that while they do provide an air cushion, they do not provide for the adjustment of pressure precisely where it is needed by the amputee in order to achieve the greatest degree of comfort and yet obtain completely stable and firm attachment of the prosthesis to the residual limb.

SUMMARY OF THE INVENTION

The prosthetic appliance of this invention comprises a prosthesis member having a cavity at its upper or proximate end formed of a rigid material and a socket member formed of a flexible material and nested within the cavity of the prosthesis member.

It has been found that in order to achieve the greatest comfort for a residual limb in a prosthetic appliance the amputee have instant, separate and independent adjustment control over at least two pressure points between the artificial limb and the residual limb. In order to accomplish this, a plurality of separate bladders are provided, preferably between the socket member and the prosthesis shell with means for manually and separately inflating or deflating each of these several bladders, so that the amputee may adjust the pressure between the appliance and the residual limb.

It is preferred that there be at least three separate inflatable and deflatable bladders, although, in some instances and with some amputees, it may be desirable to have more or fewer independently inflatable and deflatable bladders. The bladders are preferably placed at the interface between the hard, rigid outer shell of the prosthesis member and the substantially softer, flexible socket member, such that when the bladders are inflated they will act against the rigid prosthesis shell and force the wall of the socket member inwardly to engage and grip the artificial limb or the sock which surrounds the artificial limb. The socket member, which is softer than the outer shell of the prosthesis member, is nevertheless quite stiff and, therefore, there is no tendency to permit movement between the residual limb and the socket member once the bladders have been inflated to a comfortable level. Greater stability and comfort is achieved through the separate, independently adjustable bladders.

It is also preferred that the bladders be attached to and actually form a part of the wall of one of the members, i.e., either the outer wall of the socket member or the inner wall of the prosthesis member. It is preferred that each of the bladders have a separate pneumatic line and that there be a separate means for inflating and deflating each of the bladders through these separate lines.

BRIEF DESCRIPTION OF THE DRAWINGS

In the drawings:

FIG. 1 is a perspective view of a prosthetic device constructed in accordance with this invention, showing the socket member ready for insertion into the shell of the prosthesis member;

FIG. 2 is a perspective view and shows the prosthetic appliance after the socket member has been inserted into the shell of the prosthesis member;

FIG. 3 is a side sectional view of the prosthetic appliance taken substantially along line 3—3 of FIG. 2;

FIG. 4 is a slightly enlarged sectional view of a portion of the prosthetic appliance taken at substantially right angles to the view in FIG. 3 substantially along line 4—4 of that figure;

FIG. 5 is a sectional view taken substantially along line 5—5 of FIG 2;

FIG. 6 is a cross-sectional view of a slightly modified appliance in which the inflatable bladders are positioned on the inner wall of the shell of the prosthesis member; and FIG. 7 is a schematic illustration of one means for independently and separately inflating each of the bladders.

DETAILED DESCRIPTION OF THE PREFERRED EMBODIMENTS

The prosthetic appliance of the present invention will be described in connection with an artificial leg, but it will be appreciated that the invention will have applicability to artificial arms as well. The appliance includes a prosthesis member 10, which in this case is a below the knee artificial leg. At the upper or proximate end of the prothesis member is a hollow cavity or shell 12. The prosthesis member is molded of a rigid, relatively hard molded plastic or rubber and is of the usual and standard construction for such a prosthesis. The upper or proximate end of the prosthesis member has a cavity or shell 12 which is adapted to receive a socket member 14 formed of a soft, though somewhat stiff, flexible, resilient material which may be a foamed polyethylene having a Surlyn covering. The socket member 14 is carefully molded to fit the residual limb 16 of the amputee which is shown in dotted lines in FIG. 2. The purpose of the socket member 14 is to provide a comfortable cushion between the residual limb 16 and the hard shell 12 of the prosthesis member.

Both the fit of the socket member 14 onto the artificial limb 16 and the fit of that socket 14 into the shell 12 of the prosthesis member 10 are very important and must be exacting because the prosthesis has to be firmly attached to the residual limb and yet it must be comfortable over an extended period of time. The solutions of the past, which have included the insertion of padding into the shell of the prosthesis member or the applying of inflatable cushioning simply did not solve the problems of user comfort and firm attachment of the appliance to the residual limb.

In accordance with this invention, there is attached to the flexible socket 14 a plurality of inflatable bladders 18. In the present instance, there are four such bladders 18a, 18b and 18c, which are distributed around the exterior side walls of the socket 14 and a bottom bladder 18d, which is located at the bottom of the socket 14. The exact placement of each of the bladders 18 may vary slightly for each amputee and in many instances the bottom bladder 18d may be eliminated.

The bladders 18 are formed of a resilient film or composite sheet of the type used to make inflatable mattresses or inflatable air bags in automobiles. In the particular embodiment illustrated, the bladders are built into the exterior side wall of the socket member 14 and, thus, engage the interior side wall of the cavity defining shell 12, as shown in FIGS. 3-5. An important feature of this invention is that the bladders are separate from one another, and they are each independently inflatable so that the amount of the inflation may be adjusted. To this end, each of the bladders has a pneumatic hose or inflation conduit. Thus, inflation conduit 20 extends from the right front bladder 18a, conduit 21 extends from the rear or anterior bladder 18b, conduit 22 extends from the left front bladder 18c (see FIG. 3), and conduit 23 extends from the bottom bladder 18d.

The conduits 20-23 are connected to the inlet ports 24 of a valve body 26. The valve body as will be more fully explained may contain four independently operable, normally-closed inlet valves and four normally closed exhaust valves, all of standard and well-known construction. The exhaust valves are each connected to one of the pneumatic conduits 20-23 and are operated and controlled by valve operating members 28a-d, respectively. The operating members 28a-d when pressed inwardly, open the associated valve to relieve the pressure in the respective bladders to which the conduits 20-23 lead.

At the side of the valve body 26 opposite the outlet ports 24, there are four inlet ports 30a-d best seen in FIG. 2, with inlet port 30a leading to conduit 20, inlet port 30b leading to leading to conduit 21, inlet port number 30c leading to conduit 22 and inlet port number 30d leading to conduit 23. Communicating with the inlet ports 30a-d is a manually operable air pump means 32. This air pump means could be a finger pump of the type disclosed in U.S. Pat. No. 4,655,779, in which case a separate finger pump would be attached to each of the four inlet ports. Alternatively a single large squeeze bulb-type air pump can be provided which can be moved from one inlet port to the other. The particular air pump shown has a resilient rubber-like squeeze bulb 34 at one end of which is a nozzle 36 and at the other end is a one-way valve 38 of well-known construction. The valve 38 allows air to enter the bulb 34 but not to exit. The nozzle 36 of the air pump means is insertable selectively into one of the inlet ports 30a-d of the valve body 26, as best shown in FIGS. 2 and 3. In FIG. 2, the nozzle of the pump is inserted into the first or top inlet port 30a, and in FIG. 3, it is inserted into the bottom or fourth inlet port 30d. Thus, the pump can be moved from one inlet port to the other to force air through the particular inlet port into the particular conduit, which is associated with that port.

In FIG. 7 there is illustrated schematically one form of means for selectively inflating and deflating each of the bladders. Within the valve body 26 at each of the inlet ports 30a-d, there is a one-way valve 40 which allows air to enter the inlet port from the nozzle 36 of the squeeze bulb 34 but prevents air from escaping. This is of well-known construction and may be similar to the valve 38 at the end of the squeeze bulb 34. Downstream from the valve 40 is an exhaust line 42 having a normally closed exhaust valve 44 which may be opened by depressing the associated operating member 28a as previously explained. Each bladder may be independently inflated by inserting the nozzle of the squeeze bulb 34 into the selected inlet port and squeezing the bulb several times. Each bladder may be independently exhausted by depressing the particular operative member 28a-d controlling the conduit leading to that particular bladder.

For example, in order to pump air into the conduit 21 which inflates the rear or anterior bladder 18b, the nozzle 36 of the squeeze bulb 24 is inserted into port 30c and the squeeze bulb is repeatedly squeezed to pump air through this conduit unto the bladder 18b. If it is desired to release some of the pressure and thus partially or wholly deflate the bladder 18b, the valve operating member 28b may be depressed, thus, relieving the pressure and releasing the air from the conduit 21 and the bladder 18b.

In like manner, the other bladders may be individually inflated or deflated to achieve the desired pressure of the bladder on the socket 14. Each of the bladders will act against the rigid interior wall of the cavity defining shell 12 and will gently force the portion of the resilient socket 14 inwardly to grip the residual limb 16. The amputee user may adjust the pressure in each of the bladders 18 independently and separately in order to achieve the greatest degree of comfort in the securement of the prosthesis member 10 and socket member 14 to the residual limb 16. The placement of the bladders will vary from person to person, but the bladders are not only independently inflatable and totally separate from one another, but they are preferably suitably spaced around the interface between the cavity defining shell 12 of the prosthesis 10 and the inserted socket 14 so that when they are individually and separately inflated, they will firmly and yet comfortably grip the residual limb.

FIG. 6 shows a slight modification in the arrangement of the bladders 18. Here, the bladders 18a', 18b', and 18c' are positioned identically to that previously described and illustrated best in FIG. 5. However, in this embodiment, instead of being formed into the exterior side wall of the socket member 14, these bladders are formed into the interior of the cavity defining shell 12 of the prosthesis member 10.

The bladders 18 are arranged so that when inflated they act will against the rigid prosthesis wall and force the soft, flexible, resilient wall of the socket 14 inwardly to grip the residual limb 16. The bladders preferably are secured to and form a part of the wall of one of the members, i.e., either the socket member 14 or the prosthesis member 10. This prevents any shifting of the individual bladders. The socket member wall is relatively soft and flexible compared to the prosthesis wall and, thus, the socket wall will move inwardly to grip the residual limb when one or more of the bladders are inflated. The socket wall, however, is somewhat preferably stiff, and this prevents movement between the bladder and the residual limb such as might be experienced if the bladder were actually in contact with the limb.

With the particular air pump means and valve means illustrated, it is convenient to secure the valve body 26 to the exterior of the prosthesis member by means of a velcro attachment. One piece of velcro 46 may be adhesively attached to the outer wall at the top of the prosthesis member 10, as shown in FIG. 1, and the other piece of velcro (not shown) may be attached to the inside of the valve body 26, so that when the velcro on the valve body is brought into contact with the velcro 46 on the prosthesis member 10, the valve body 26 will adhere thereto. This is a particularly good arrangement with the embodiment of FIGS. 1-5 since the socket member 14 to which the bladders 18 are attached must be separable from the prosthesis member 10. In the embodiment of FIG. 6, however, where the bladders 18 are attached to the interior wall of the cavity-defining shell 12 of the prosthesis member 10, it may in some instances be desirable to permanently attach the valve body to the exterior of the prosthesis.

It will be appreciated that other manually operable pump means may be provided and the valve means may be one of many different types of well-known construction. It would be possible to even have a compressed gas source of pressurization for the bladders, although this is less preferred than the air pump. The removable air pump illustrated has the advantage that it can be removed and kept in the users pocket and it can be easily operated by the user when it is necessary to inflate one or more of the bladders to a greater or lesser extent. The valves described are only examples of a wide variety of valves which can be employed.

The foregoing description has been given only by way of example and numerous modifications may be made as will readily appear to those skilled in the art without departing from the spirit and scope of the invention as hereinafter claimed.

What is claimed is:

1. A prosthetic appliance for a residual limb, said appliance comprising a prosthesis member having a cavity at its proximate end defined by sidewalls formed of a rigid molded material; a separate removable molded socket member having sidewalls formed of a flexible material, said socket member being nested within the cavity of said prosthesis member, said socket member being adapted to receive the residual limb; a plurality of separate, independently inflatable bladders disposed at predetermined intervals between the sidewalls of said prosthesis member and the sidewalls of said socket member and being attached to one of said members, said bladders when inflated acting against the other of said members to resiliently force discrete portions of the socket member sidewalls inwardly to grip the residual limb; and inflation control means including at least one air pump and at least one valve for selectively inflating and deflating each of said bladders separately and independently to achieve a comfortable and independently variable gripping pressure on the residual limb at each of the predetermined intervals.

2. The prosthetic appliance of claim 1 wherein said socket is a resilient and flexible soft foam.

3. A prosthetic appliance for a residual limb, said appliance comprising a prosthesis member having a cavity at its proximate end defined by sidewalls formed of a rigid molded material; a separate removable molded socket member having sidewalls formed of a flexible material, said socket member being nested within the cavity of said prosthesis member being adapted to receive the residual limb; a plurality of separate, independently inflatable bladders disposed at predetermined intervals between the sidewalls of said prosthesis member and the sidewalls of said socket member and being attached to one of said members, said bladders when inflated acting against the other of said members to resiliently force discrete portions of the socket member sidewalls inwardly to grip the residual limb; and inflation control means comprising at least one manually operable air pump and a plurality of manually operable air valves, one for each of said bladders, for selectively inflating and deflating the associated bladder separately and independently of the other bladders, whereby the gripping pressure on the residual limb at each discrete portion of the socket member may be adjusted separately and independently by both said air pump and said air valves.

* * * * *